(12) United States Patent
Koo et al.

(10) Patent No.: US 10,052,405 B2
(45) Date of Patent: Aug. 21, 2018

(54) BIODEGRADABLE IMPLANT AND METHOD FOR MANUFACTURING SAME

(71) Applicant: U&I Corporation, Gyeonggi-do (KR)

(72) Inventors: Ja-Kyo Koo, Seoul (KR);
Hyun-Kwang Seok, Seoul (KR);
Seok-Jo Yang, Daegu (KR); Yu-Chan Kim, Seoul (KR); Sung-Youn Cho, Uijeongbu-si (KR); Jong-Tack Kim, Jeonju-si (KR)

(73) Assignee: U&I Corporation, Gyeonggi-do (KR)

(*) Notice: Subject to any disclaimer, the term of this patent is extended or adjusted under 35 U.S.C. 154(b) by 0 days.

(21) Appl. No.: 14/824,644

(22) Filed: Aug. 12, 2015

(65) Prior Publication Data
US 2016/0000964 A1      Jan. 7, 2016

Related U.S. Application Data

(62) Division of application No. 13/265,694, filed as application No. PCT/KR2010/002542 on Apr. 22, 2010, now abandoned.

(30) Foreign Application Priority Data

Apr. 22, 2009  (KR) .................. 10-2009-0035267

(51) Int. Cl.
*A61F 2/28* (2006.01)
*A61L 27/04* (2006.01)
(Continued)

(52) U.S. Cl.
CPC .......... *A61L 27/047* (2013.01); *A61L 27/42* (2013.01); *A61L 27/427* (2013.01);
(Continued)

(58) Field of Classification Search
CPC .................. A61F 2/28; C22C 23/00
See application file for complete search history.

(56) References Cited

U.S. PATENT DOCUMENTS 8,002,821 B2   8/2011  Stinson
8,293,031 B2  10/2012  Gerold et al.
(Continued)

FOREIGN PATENT DOCUMENTS

JP       2007-215620 A     8/2007

OTHER PUBLICATIONS

Guangling Song, "Control of biodegradation of biocompatable magnesium alloys", ScieneDirect, Corrosion Science 49 (2007), pp. 1696-1701, Cooperative Research Centre, School of Engineering, The University of Queensland, St. Lucia, Brisbane, Qld 4072, Australia.

(Continued)

*Primary Examiner* — Bruce E Snow
(74) *Attorney, Agent, or Firm* — Blank Rome LLP

(57) ABSTRACT

This invention relates to a biodegradable implant including magnesium, wherein the magnesium contains, as impurities, (i) manganese (Mn); and (ii) one selected from the group consisting of iron (Fe), nickel (Ni) and mixtures of iron (Fe) and nickel (Ni), wherein the impurities satisfy the following condition: $0<(ii)/(i)\leq 5$, and an amount of the impurities is 1 part by weight or less but exceeding 0 parts by weight based on 100 parts by weight of the magnesium, and to a method of manufacturing the same.

13 Claims, 13 Drawing Sheets

(51) Int. Cl.
| | |
|---|---|
| A61L 27/42 | (2006.01) |
| A61L 27/48 | (2006.01) |
| A61L 27/56 | (2006.01) |
| A61L 27/58 | (2006.01) |
| C22C 23/00 | (2006.01) |
| C22F 1/06 | (2006.01) |
| A61L 27/44 | (2006.01) |
| C22C 23/02 | (2006.01) |
| B22F 3/11 | (2006.01) |
| B22F 3/26 | (2006.01) |
| B22F 7/06 | (2006.01) |

(52) U.S. Cl.
CPC .............. *A61L 27/446* (2013.01); *A61L 27/48* (2013.01); *A61L 27/56* (2013.01); *A61L 27/58* (2013.01); *B22F 3/1121* (2013.01); *B22F 3/26* (2013.01); *B22F 7/06* (2013.01); *C22C 23/00* (2013.01); *C22C 23/02* (2013.01); *C22F 1/06* (2013.01); *B22F 2998/10* (2013.01); *Y10T 29/49* (2015.01)

(56) References Cited

U.S. PATENT DOCUMENTS

| | | | |
|---|---|---|---|
| 2003/0000608 A1* | 1/2003 | Horie | C22C 23/04 |
| | | | 148/666 |
| 2009/0024209 A1 | 1/2009 | Ozdil et al. | |
| 2011/0313527 A1 | 12/2011 | Witte et al. | |

OTHER PUBLICATIONS

Zijian Li, et al., "The development of binary Mg—Ca alloys for use as biodegradable materials within bone", ScienceDirect, Biomaterials 29 (2008), pp. 1329-1344, LTCS, College of Engineering, Peking University, Beijing 100871, China, Department of Orthopedics, Peking University Third Hospital, Beijing 100083, China.

Woo-Cheol Kim et al., "Influence of Ca on the corrosion properties of magnesium for biomaterials", Materials Letters, 2008, pp. 4146-4148, vol. 62, Department of Advanced Materials Engineering, Sunkyunkwan University, 300 Chunchun-Dong, Jangan-Gu, Suwon 440-746.

* cited by examiner

BIODEGRADABLE IMPLANT AND METHOD FOR MANUFACTURING SAME

CROSS-REFERENCE TO RELATED APPLICATIONS

This application is a divisional of U.S. patent application Ser. No. 13/265,694, filed on Oct, 21, 2011, the subject matter of which is incorporated in its entirety by reference herein. U.S. patent application Ser. No. 13/265,694 was the U.S. National Stage of International Application No. PCT/KR10/02542, filed Apr. 22, 2010, the subject matter of which is also incorporated in its entirety by reference herein.

TECHNICAL FIELD

The present invention relates to a biodegradable implant and a method of manufacturing the same, and more particularly to a biodegradable implant, whose biodegradation rate is easily controlled, the strength and an interfacial force to bone tissue of which are high, in which a rate of bone formation is increased, and that has simultaneously improved corrosion resistance and mechanical properties, and to a method of manufacturing the same.

BACKGROUND ART

Typical materials used in implants to be used in medical treatment include metal, ceramic and polymer. Among these, metallic implants have superior mechanical properties and processability. However, metallic implants are disadvantageous because of stress shielding, image degradation and implant migration. Also, ceramic implants have superior biocompatibility compared to the other implants. However, ceramic implants are easily broken by external impact, and are difficult to process. Also, polymeric implants have relatively weak strength compared to the other implant materials.

Recently, porous implants are being developed which may accelerate the formation of bone tissue upon insertion into the human body and may decrease Young's modulus to prevent stress shielding. However, such porous implants have low mechanical strength and are weak to external impact. Also, research and development is being carried out into biodegradable implants which need not be removed after being inserted into the human body to achieve their desired purpose. The study of medical applications using such a biodegradable material has already begun since the middle of the 1960s and is mainly focused on using polymers such as polylactic acids (PLA), polyglycolic acid (PGA) or a copolymer thereof including PLGA. However, biodegradable polymers have low mechanical strength, produce acids upon decomposition, and have the disadvantage that it is difficult to control their biodegradation rate, and thus they have limited applications. In particular, the biodegradable polymers are difficult to apply to orthopedic implants that have to withstand a strong load or dental implants because of the properties of polymers having low mechanical strength. Hence, some biodegradable materials are being studied to overcome the problems of the biodegradable polymers. Typical examples thereof include ceramic such as tri-calcium phosphate (TCP), combination materials of biodegradable polymer and biodegradable hydroxyapatite (HA), etc.

However, mechanical properties of such materials are not much higher than those of biodegradable polymers. In particular, poor impact resistance of the ceramic material is regarded as very disadvantageous in a biomaterial. Also, the actual usability of such materials is open to question, because it is difficult to control the biodegradation rate.

Meanwhile, biodegradable implants should be very strong because part or all of it have to withstand a load when used into the human body. In order to ensure high strength, a biodegradable implant is further subjected to additional processes including rapid cooling, extrusion, and heat treatment so that the framework of the implant is made fine and internal residual stress should be controlled. Also, the alloy composition of a metal used for a biodegradable implant should be appropriately designed by changing constituent elements or content thereof. As such, changing the alloy composition may be typically performed by adjusting the amounts of the elements that are added. As the amounts of elements added to the alloy increase, mechanical strength is enhanced.

However, when the amounts of added elements are increased, the metal for the implants may easily create a galvanic circuit that increases the corrosion rate attributable to an increase in the non-uniformity of the composition thereof and the non-uniformity of a fine framework, undesirably increasing the corrosion rate of implants. Hence, it is very difficult to design alloy materials which have high strength and low biodegradation rate to be applied to implants.

DISCLOSURE

Technical Problem

Accordingly, the present invention has been made keeping in mind the above problems occurring in the related art, and an object of the present invention is to provide a biodegradable implant whose biodegradation rate may be controlled.

Another object of the present invention is to provide a biodegradable implant which may overcome problems of conventional porous implants such as low mechanical strength and poor impact resistance.

A further object of the present invention is to provide a biodegradable implant whose corrosion resistance and mechanical properties have been simultaneously improved.

Still a further object of the present invention is to provide a biodegradable implant in which a rate of bone formation may be increased, and with the passing of a predetermined period of time after surgery, a biodegradable metal material charged in pores has disappeared and an osseous replacement has taken place.

Technical Solution

In order to accomplish the above objects, an aspect of the present invention provides a biodegradable implant comprising magnesium, wherein the magnesium contains as impurities (i) manganese (Mn); and (ii) one selected from the group consisting of iron (Fe), nickel (Ni) and mixtures of iron (Fe) and nickel (Ni), wherein the impurities satisfy the following condition: $0<(ii)/(i)\leq 5$, and an amount of the impurities is 1 part by weight or less but exceeding 0 parts by weight based on 100 parts by weight of the magnesium.

In addition, another aspect of the present invention provides a method of manufacturing a biodegradable implant, comprising a) providing magnesium containing as impurities (i) manganese (Mn); and (ii) one selected from the group consisting of iron (Fe), nickel (Ni) and mixtures of iron (Fe) and nickel (Ni), wherein the impurities satisfy the following condition: $0<(ii)/(i)\leq 5$, and an amount of the impurities is 1 part by weight or less but exceeding 0 parts by weight based on 100 parts by weight of the magnesium; and b) forming the magnesium.

In addition, another aspect of the present invention provides a biodegradable implant, comprising a magnesium alloy represented by Chemical Formula 1 below comprising based on the total weight thereof, 23 wt % or less but exceeding 0 wt % of Ca; 10 wt % or less but exceeding 0 wt % of X; and a remainder of Mg:

Mg—Ca—X          <Chemical Formula 1> wherein X is Mn or Zn.

In addition, another aspect of the present invention provides a method of manufacturing a biodegradable implant, comprising i) providing the magnesium alloy; and ii) forming the magnesium alloy.

In addition, another aspect of the present invention provides a method of manufacturing a biodegadable implant, comprising applying ultrasound to the biodegradable implant comprising magnesium.

In addition, another aspect of the present invention provides a biodegradable implant, comprising, based on the total weight thereof, 10 wt % or less but exceeding 0 wt % of manganese; 1 wt % or less but exceeding 0 wt % of iron; and a remainder of a metal comprising magnesium.

In addition, another aspect of the present invention provides a biodegradable implant, comprising, based on the total weight thereof; 90 wt % or less but exceeding 0 wt % of magnesium oxide (MgO); and a remainder of a metal comprising magnesium.

Advantageous Effects

According to the present invention, a biodegradable implant can be advantageously present for a long period of time in vivo because its biodegradation rate is controlled to be very low.

Also according to the present invention, in the case where the biodegradable implant includes a porous structure, blood vessels that pass through pores are formed, thus increasing the rate of bone formation and decreasing Young's modulus thereby reducing stress shielding.

Also according to the present invention, the biodegradable implant can have enhanced mechanical strength and impact resistance.

Also according to the present invention, the biodegradable implant can be simultaneously improved in terms of corrosion resistance and mechanical properties.

Thus, the implant according to the present invention is adapted to be used in bone replacements or treatment for bone, and can be used for orthopedics, dental care, plastic surgery or blood vessels.

BEST MODE

Figure 1:
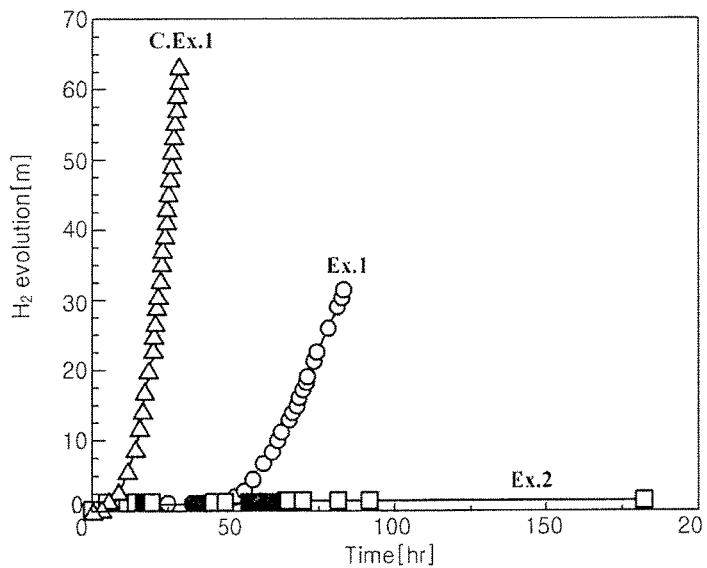
FIG. 1 is a graph showing the hydrogen evolution amount in relation to the immersion time of the implant samples of Example 1 and 2 and Comparative Examples 1.

Hereinafter, a detailed description will be given of the present invention.

I. Biodegradable Implant Containing Impurities

According to the present invention, a biodegradable implant comprises magnesium (Mg), wherein the Mg contains, as impurities (i) Mn and (ii) one selected from the group consisting of Fe, Ni and mixtures of Fe and Ni, wherein the impurities satisfy the following condition: $0<(ii)/(i)\leq 5$, and an amount of the impurities is 1 part by weight or less but exceeding 0 parts by weight based on 100 parts by weight of the magnesium.

Preferably, the impurities satisfy the following condition: $0<(ii)/(i)\le 0.5$. If the impurities satisfy the condition, the biodegradation rate is controlled to be maximally low thus increasing corrosion resistance. Thereby, implants may be present for a longer period of time in vivo.

When Ni and Mn are contained in the impurities, Ni causes an allergic reaction in the human body and increases the corrosion rate of pure Mg. Hence, Ni content is preferably 100 ppm or less, and more preferably 50 ppm or less.

Also, the Mg may further include aluminum (Al) as an impurity.

According to the present invention, there may be provided a biodegradable implant resulting from charging Mg containing the above impurities in the pores of a porous structure.

The pores of the porous structure preferably have a size of 200~500 μm, and the pore size may be adjusted depending on the application field using methods typically used in the art. If the pore size falls within the above range, it is easy to allow blood vessels responsible for supplying nutrients, minerals and ions to pass through the pores.

The porous structure may have a porosity of 5~95%. The porosity means a volume ratio of pores relative to total volume. In the case where the strength required of a target is high, the porosity may be decreased so that the strength of a porous structure is enhanced. For example, the case where a porous structure is made of tantalum having high strength or merely functions to fill the cavities of lost bone, high porosity thereof does not cause problems.

The porous structure may comprise one or more selected from the group consisting of a metal, a ceramic, and a polymer. In the case where the porous structure is made of a metal, one or more selected from the group consisting of titanium or a titanium alloy, a cobalt-chromium alloy and stainless steel may be used. In the case where the porous structure is made of a ceramic, one or more selected from the group consisting of calcium phosphate, alumina, zirconia and magnesia may be used. In the case where the porous structure is made of a polymer, one or more selected from the group consisting of polyethylene, polylactic acids (PLA), polyglycolic acid (PGA) and a copolymer thereof including PLGA may be used. As such, in the case where the porous structure may comprise the above polymer, an acid that is biodegradable is generated so that the pH may decrease. In the case of a polymer composite in which pores are filled with Mg, Mg may increase the pH while it is decomposing, and thus when the rate of decomposition of the polymer and Mg is controlled, an additional effect of arbitrarily adjusting the pH in vivo may be expected.

According to the present invention, the biodegradable implant may be used for orthopedics, dental care, plastic surgery or blood vessels. Specifically, the above implant may be utilized for an interbody spacer for the spine, a bone filler, a bone plate, bone pin, bone screw, scaffold, Stent and artificial dental root.

II. Method of Manufacturing the Biodegradable Implant Containing Impurities

Below is a description of a method of manufacturing the biodegradable implant according to the present invention.

According to the present invention, the method of manufacturing the biodegradable implant comprises a) providing Mg containing as impurities (i) Mn and (ii) one selected from the group consisting of Fe, Ni and mixtures of Fe and Ni, wherein the impurities satisfy the following condition: $0<(ii)/(i)\le 5$, and an amount of the impurities is 1 part by weight or less but exceeding 0 parts by weight based on 100 parts by weight of the magnesium; and b) forming the magnesium.

In a), Mg is preferably provided in the form of being molten. Specifically, a) is performed by melting Mg in an inert gas atmosphere such as argon (Ar) that does not react with Mg or in a vacuum. Also, providing the molten Mg in a) may be carried out using a variety of processes, including a resistance heating process for generating heat by applying electricity to a resistor, an induction heating process that allows current to flow in an induction coil, or a laser- or focused light-based process. Among the above melting processes, a resistance heating process is particularly useful. It is preferred that the molten alloy (i.e. a melt) be stirred so that the impurities are well mixed when the Mg melts.

According to another embodiment of the present invention, in the case where there is provided a biodegradable implant obtained by filling the pores of a porous structure with the Mg alloy, a) may include a-1) preparing a porous structure; and a-2) filling the pores of the porous structure with the Mg alloy.

In a-1), the porous structure may comprise one selected from the group consisting of a metal, a ceramic and a polymer.

a-1) is described below for the case when the porous structure is prepared using only a metal.

Specifically, a metal is prepared in the form of powder or a wire. The metal powder or wire is prepared into a preform (a Green preform). As such, the preform may be obtained using a sintering process or a modified sintering process.

The production of the preform using a sintering process is as follows: first, metal powder or wire is placed in a vessel, or is pressed by an appropriate force of 100 MPa or less so as to have weak strength, after which the metal having weak strength is maintained at a temperature of $2/10 \sim 9/10$ of the melting point of the metal so that the powder or wire respectively coheres thus obtaining a preform having mechanical strength.

Also, the production of the preform using a modified sintering process is as follows: first, metal powder or wire is placed in a conductive vessel such as graphite vessel, and high current is then applied to the conductive vessel so that heat is instantly generated on the contact portion of the metal powder or wire thus preparing a sintered body, which is then formed into a preform.

a-1) is described below for the case of using a metal and a polymer to prepare the porous structure.

Specifically, a metal is prepared in the form of powder or a wire. Subsequently, the metal powder or wire is mixed with a polymer, and in the course of increasing the temperature, the polymer decomposes and disappears at low temperature and the metal powder or wire is sintered at high temperature, thus obtaining a preform having the appropriate mechanical strength. As such, the porosity and the strength of the sintered body are determined by the sintering temperature, the pressure, the ratio of the polymer and metal in the mixture, etc., and proper conditions may be selected as necessary. The sintering temperature may vary depending on the type of material used to prepare the porous structure, and is typically set to the level of about $1/2 \sim 9/10$ of the melting point of the porous structure. Although sintering may occur even in the absence of pressure, sintering may rapidly progress in proportion to an increase in pressure. However, as the pressure is higher, there is a need for additional costs including device cost and mold cost, and thus the appropriate pressure should be selected.

In addition to the above method, a-1) is described below for the case of using a metal and a polymer to prepare the porous structure.

Specifically, the surface of a polymer is plated with a precious metal, such as gold, platinum, and Pd. Subsequently, the polymer is removed, thus obtaining a metal porous structure having better biocompatibility.

a-1) is described below for the case of using an aqueous salt and a metal to prepare the porous structure.

Specifically, an aqueous salt and metal powder are mixed and then formed at high temperature, thus obtaining a preform. The aqueous salt may include one or more selected from the group consisting of $NaNO_2$, $KNO_2$, $NaNO_3$, NaCl, CuCl, $KNO_3$, KCl, LiCl, $KNO_3$, $PbCl_2$, $MgCl_2$, $CaCl_2$ and $BaCl_3$.

Subsequently, the preform is pressed at a temperature of 2/10 ~9/10 of the melting point of the metal powder. In the course of pressing, the metal powder coheres via migration of atoms to form a structure, and the aqueous salt is contained therein, thus obtaining a composite. When the composite is immersed in water, only the aqueous salt may dissolve, resulting in a metal porous structure having pores. Furthermore, a metal porous structure may be obtained by completely melting a metal material and then injecting a foaming agent to generate gas.

a-1) is described below for the case when a polymer and an electrolyte having metal ions are used to prepare the porous structure.

Specifically, the surface of a porous polymer is plated with a metal using an electrolyte having metal ions. As such, the metal ions are not particularly limited, but one or more selected from the group consisting of Ti, Co, Cr and Zr may be used. Subsequently, the temperature is increased to remove the polymer, thereby obtaining a metal porous structure.

a-2) is described below for the case when the porous structure is prepared using a ceramic.

Specifically, fine ceramic grains and a binder polymer are mixed. The resultant mixture is applied on the surface of a backbone structure made of a foaming agent such as polyurethane which is removable, and then dried thus preparing a porous structure. Thereafter, when the temperature is increased, the polymer is combusted and removed at a temperature near the combustion temperature of the binder polymer. When the temperature is further increased, the remaining ceramic grains are mutually sintered, resulting in a porous structure having mechanical strength.

As such, the fine ceramic grains may comprise one or more selected from the group consisting of hydroxyapatite (HA), zirconia and alumina.

a-1) may be a modification or combination of the above methods of producing the porous structure, or may be a method of forming a porous structure having different porosities inside and outside by applying it to some of heterogeneous materials. The latter method enables the production of a porous structure the density of the inside of which is high because there are few or no pores and the porosity of the outside of which is high so that the porosity is different at different positions. This method may be employed upon production of an implant that may endure high external stress throughout its entirety while inducing a high rate of bone formation on the surface of the implant. Furthermore, the production of the porous structure as above is only an illustration among a variety of methods of producing a porous structure, and the scope of the present invention is not limited by variations of the methods of producing the porous structure.

a-2) may include one selected from the group consisting of immersing the porous structure in a molten Mg solution, allowing a molten Mg solution to flow in the fixed porous structure so that pores are filled therewith, and applying an external pressure of 1 atm or more in the above two cases so that molten Mg is more easily charged in the pores of the porous structure. As such, in order to prevent the molten Mg from solidifying in the course of the pores being filled therewith, the porous structure may be heated or a variety of surface contaminants may be removed so that the molten Mg is easily charged in the pores.

Also, a-2) may be as follows: Mg is vaporized at high temperature, preferably 700° C. or more, so that Mg vapor is deposited on the surface of the pores while passing through the pores of the porous structure, thus filling the pores of the porous structure with Mg.

Also, a-2) may be as follows: an Mg-containing salt is melted in a liquid, after which Mg is adsorbed on the surface of the pores of a porous structure while passing the porous structure through the liquid.

As another modification in addition to the above filling processes, only part of pores of the porous structure may be filled with the Mg alloy, instead of all of them being filled therewith. Specifically, the molten Mg is charged in the porous structure, after which high-pressure gas is blown into the porous structure or the porous structure is rotated or stirred before Mg is completely solidified. Thereby, non-solidified Mg is removed from the porous structure and only part of Mg may be left behind in the pores, thus obtaining a composite in which part of the pores is impregnated with Mg. In this case, a rate of charging Mg may be differently controlled at positions of the pores of the porous structure.

As another modification, the application of Mg is controlled such that Mg is applied only to the surface of the backbone of the porous structure and a predetermined portion of the pores may remain unfilled, and thereby additional effects are expected including it being easier to form bone by Mg while maintaining spaces wherein the fine blood vessels necessary to form bone may be easily formed in the implant.

In the case of a polymer having a melting point lower than that of Mg, when a porous structure is first prepared and then pores thereof are filled with molten Mg, the polymer porous structure cannot maintain its shape. Thus, the biodegradable polymer having a polymer and Mg may be manufactured by mixing Mg powder and the polymer at a volume ratio of 5:95 to 95:5, increasing the temperature to 150~500° C. and applying pressure in the range of 1 atm to 100 atm. The above conditions are preferable for the manufacture of the polymer-Mg biodegradable implant, but under conditions falling outside of the above conditions, the polymer-Mg biodegradable implant may also be formed. Thus it will infringe the scope of the present invention to change the manufacturing conditions for manufacturing the polymer-Mg biodegradable implant.

The method of manufacturing the porous structure made of metal, ceramic and polymer, the method of filling pores of the porous structure with Mg alloy, and the method of manufacturing the Mg-filled polymer biodegradable implant are merely illustrative in the present invention, and the scope of the present invention is not limited thereto.

In the method of manufacturing the biodegradable implant according to the present invention, b) may be forming the molten Mg alloy for controlling a biodegradation rate using one or more selected from the group consisting of cooling, extrusion and metal processing.

The cooling process may be used to enhance the mechanical strength of the Mg alloy. Specifically, when Mg is melted in a), immersing a crucible including molten Mg in water may be utilized. Also, the molten Mg may be cooled by spraying an inert gas such as argon. The cooling process using spraying is performed at a much higher rate thus obtaining a very fine framework. However, in the case where Mg is cast in a small size, it should be noted that a plurality of pores (black portion) be formed therein.

The extrusion process is used to make the framework of the Mg uniform and enhance mechanical performance. The extrusion process may be performed at 300~450° C. Furthermore, the extrusion of Mg may be carried out in a ratio of reduction in the cross-sectional area before and after extrusion (an extrusion ratio) of 10:1~30:1. As the extrusion ratio becomes higher, the fine framework of the extrusion material may become uniform, and defects caused upon casting may be easily removed. In this case, it is preferred that the capacity of an extrusion device be increased.

The metal processing is not particularly limited so long as it is known in the art. For example, molten Mg may be poured onto a mold processed to have a shape close to a shape of a final product and thus directly cast, or may be prepared into an intermediate material such as a rod or a sheet and then subjected to turning or milling, and also the Mg alloy may be forged at a higher pressure thus obtaining a final product.

III. Biodegradable Implant Represented by Mg—Ca—X

The biodegradable implant according to the present invention comprises an Mg alloy which is represented by Chemical Formula 1 below and comprises based on the total weight thereof, 23 wt % or less but exceeding 0 wt % of Ca, 10 wt % or less but exceeding 0 wt % of X, and a remainder of Mg.

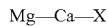     <Chemical Formula 1>

In Chemical Formula 1, X is Mn or Zn.

When the Mg alloy falls within the above range, a biodegradable implant in which mechanical properties and corrosion resistance are simultaneously improved and brittleness fractures do not occur may be provided.

Also, the Mg alloy preferably comprises, based on the total weight thereof, 23 wt % or less but exceeding 0 wt % of Ca, 0.1~5 wt % of X and the remainder of Mg, and more preferably 23 wt % or less but exceeding 0 wt % of Ca, 0.1~3 wt % of X and the remainder of Mg. When the same corrosion rate is embodied, the case where the amount of impurities is low is favorable for fear of the impurities causing side effects.

According to the present invention there may be provided a biodegradable implant obtained by filling pores of a porous structure with the Mg alloy represented by Chemical Formula 1, comprising, based on the total weight thereof, less than 23 wt % but exceeding 0 wt % of Ca, less than 10 wt % but exceeding 0 wt % of X, and a remainder of Mg.

The size of pores of the porous structure is preferably 200~500 μm. The pore size may be adjusted depending on the application field using typical methods of the art. When the pore size falls within the above range, it is easy to allow blood vessels responsible for supplying nutrients, minerals and ions to pass through the pores.

The porous structure may have a porosity of 5~95%. The porosity is a volume ratio of pores relative to total volume. In the case where the required strength of a target is high, the porosity is decreased so that the strength of the porous structure may be increased. For example, the case where the porous structure is a metal such as tantalum having high strength or merely functions to fill the cavities of lost bone, high porosity thereof does not cause problems.

The porous structure may be formed of one or more selected from the group consisting of a metal, a ceramic and a polymer. The metal may include one or more selected from the group consisting of titanium or a titanium alloy, a cobalt-chromium alloy and stainless steel. The ceramic may include one or more selected from the group consisting of calcium phosphate, alumina, zirconia and magnesia. The polymer may include one or more selected from the group consisting of polyethylene, polylactic acids (PLA), polyglycolic acid (PGA) and a copolymer thereof such as PLGA. In the case where the porous structure is made with the above polymer, a biodegradable acid may be produced thus decreasing the pH. As such, in the case of a polymer composite comprising pores filled with the Mg alloy, Mg may increase the pH while it is decomposing, and thus an additional effect of arbitrarily adjusting the pH in vivo via control of the rate of decomposition of the polymer and Mg may be expected.

The biodegradable implant according to the present invention may be used for orthopedics, dental care, plastic surgery or blood vessels. Specifically, the above implant may be utilized for an interbody spacer for the spine, a bone filler, a bone plate, bone pin, bone screw, scaffold, and artificial dental root.

IV. Method of Manufacturing the Biodegradable Implant Represented by Mg—Ca—X

Below is a description of a method of manufacturing the biodegradable implant according to the present invention.

The biodegradable implant according to the present invention is manufactured by i) providing an Mg alloy represented by Chemical Formula 1 below, comprising based on the total weight thereof less than 23 wt % but exceeding 0 wt % of Ca, less than 10 wt % but exceeding 0 wt % of X, and less than 100 wt % but exceeding 67 wt % of Mg; and ii) forming the Mg alloy.

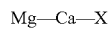     <Chemical Formula 1>

In Chemical Formula 1, X is Mn or Zn.

The description of the Mg alloy is as above and is omitted herein.

i) is preferably providing the Mg alloy in a molten state. The description of i) is the same as that of a) and is thus omitted.

According to another embodiment of the present invention, in the case where there is provided a biodegradable implant resulting from filling the pores of a porous structure with the above Mg alloy, i) may comprise i-1) preparing a porous structure and i-2) filling the pores of the porous structure with the Mg alloy.

The description of i-1) and i-2) is the same as that of a-1) and a-2) and is thus omitted.

In the method of manufacturing the biodegradable implant according to the present invention, may be forming the molten Mg alloy for controlling a biodegradation rate using one or more selected from the group consisting of cooling, extrusion and metal processing.

The description of is the same as that of b) and is thus omitted.

V. Method of Manufacturing Biodegradable Implant Using Ultrasound

The present invention provides a method of manufacturing a biodegradable implant, comprising applying ultrasound to the biodegradable implant comprising Mg. When ultrasound is applied to the biodegradable implant comprising Mg, the corrosion rate may increase in vivo, so that the implant may disappear within a shorter period of time.

The biodegradable implant comprising Mg may be a porous structure, wherein Mg contains as impurities (i) Mn and (ii) one selected from the group consisting of Fe, Ni and mixtures of Fe and Ni, wherein the impurities satisfy the following condition: 0<(ii)/(i)≤5, and an amount of the impurities is 1 part by weight or less but exceeding 0 parts by weight based on 100 parts by weight of the magnesium. Also, the biodegradable implant may include an Mg alloy represented by Chemical Formula 1 below, comprising based on the total weight thereof, less than 23 wt % but exceeding 0 wt % of Ca, less than 10 wt % but exceeding 0 wt % of X, and less than 100 wt % but exceeding 67 wt % of Mg.

  <Chemical Formula 1>

In Chemical Formula 1, X is Mn or Zn.

The biodegradable implant according to the present invention may be advantageously present in vivo for a long period of time because the biodegradation rate is controlled to be very low. Also, in the case where the biodegradable implant according to the present invention includes a porous structure, blood vessels that pass through the pores are formed, thus increasing the rate at which bone is formed and decreasing Young's modulus to thereby reduce stress shielding. Also, the biodegradable implant according to the present invention may have enhanced mechanical strength and impact resistance. Also, the biodegradable implant according to the present invention may be simultaneously improved in terms of corrosion resistance and mechanical properties. Thus, the implant according to the present invention is adapted to be used in bone replacements or treatment for bone and may be used for orthopedics, dental care, plastic surgery or blood vessels.

VI. Biodegradable Implant Having Controlled Mn Content

The biodegradable implant according to the present invention comprises, based on the total weight thereof, 10 wt % or less but exceeding 0 wt % of Mn; 1 wt % or less but exceeding 0 wt % of Fe; and 99 wt % to less than 100 wt % of a metal comprising Mg. As such, the Mn content may be set to 0.3~0.6 wt %.

In the biodegradable implant according to the present invention, Fe is further included as an impurity.

The biodegradable implant according to the present invention includes Mn in the above content range, which is bound with Fe contained in the metal comprising Mg thus decreasing a difference in potential to thereby reduce galvanic corrosion. Furthermore, Fe contained in the metal comprising Mg is enclosed with Mn so that contact between Mg and Fe is blocked, thus preventing or reducing the corrosion.

Here, the metal comprising Mg may be pure Mg, Mg having a very small amount of impurity, or an Mg alloy. This impurity X may be selected from the group consisting of zirconium (Zr), molybdenum (Mo), niobium (Nb), tantalum (Ta), titanium (Ti), strontium (Sr), chromium (Cr), manganese (Mn), zinc (Zn), silicon (Si), phosphorus (P) and nickel (Ni).

VII. Biodegradable Implant Comprising Magnesium Oxide

The biodegradable implant according to the present invention comprises, based on the total weight thereof, 90 wt % or less but exceeding 0 wt % of magnesium oxide (MgO); and 10 wt % to less than 100 wt % of a metal comprising Mg.

When MgO is contained in the above amount in the biodegradable implant according to the present invention, the corrosion properties of the biodegradable implant are controlled, thus preventing swelling due to hydrogen being generated upon insertion of the biodegradable implant in vivo.

As the amount of MgO is higher in the biodegradable implant according to the present invention, the corrosion of the metal comprising Mg may be reduced. However, it is very preferred that MgO be contained in the above amount range.

The metal comprising Mg may be pure Mg, Mg having a very small amount of impurity, or an Mg alloy. This impurity X may be selected from the group consisting of zirconium (Zr), molybdenum (Mo), niobium (Nb), tantalum (Ta), titanium (Ti), strontium (Sr), chromium (Cr), manganese (Mn), zinc (Zn), silicon (Si), phosphorus (P) and nickel (Ni).

VIII. Biodegradable Implant Having Controlled Corrosion Properties Via Extrusion The biodegradable implant according to the present invention may prevent PCP (Preferred Crystallographic Pitting Corrosion) caused by coarse crystal grains therein, using extrusion. Specifically, when crystal grains are coarse, the probability of corrosion between the crystal grains is high. The size of crystal grains is decreased via extrusion so that the intervals between crystal grains are decreased, thereby preventing such corrosion.

As such, the ratio of reduction in the cross-sectional area before and after extrusion (the extrusion ratio) is not particularly limited so long as it is 2:1 or more, but preferably exceeds 25:1 or 20:1.

Mode For Invention

The following examples which are set forth to illustrate but are not to be construed as limiting the present invention, may provide a better understanding of the present invention which is about the manufacturing of biodegradable implants comprising Mg or an Mg alloy for controlling the biodegradation rate.

EXAMPLES 1, 2 AND COMPARATIVE EXAMPLE 1

Manufacturing of Biodegradable Implant comprising Mg Alloy for Controlling Biodegradation Rate comprising 1 part by weight or less but exceeding 0 parts by weight of Total of Impurities including Mn, Fe and Ni based on 100 parts by weight of Mg and the impurities satisfying the following condition:

0<{Fe+Ni}/Mn≤5

Fe, Ni, Al, Mn and Mg in the amounts shown in Table 1 below were charged in a crucible having an inner diameter of 50 mm made of stainless steel (SUS 410). Subsequently, while Ar gas was allowed to flow around the crucible so that Fe, Ni, Mn, Al and Mg in the crucible did not come into contact with air, the temperature of the crucible was increased to about 700~750° C. inside a resistance heating furnace so that the Fe, Ni, Al, Mn and Mg melted. The crucible was stirred so that the molten Fe, Ni, Al, Mn and Mg were well mixed. The completely molten Mg alloy was cooled, thus preparing an Mg alloy in the solid phase. Also upon cooling, the crucible was immersed in water to enhance the mechanical strength of Mg, whereby the molten Mg alloy was rapidly cooled.

The Mg alloy in the solid phase was extruded at 400° C. under conditions of the ratio of reduction in the cross-sectional area before and after extrusion (the extrusion ratio) being set to 15:1.

TABLE 1

|  | Fe (wt part) | Ni (wt part) | All (wt part) | Mn (wt part) | Mg (wt part) | (Fe + Ni)/Mn |
| --- | --- | --- | --- | --- | --- | --- |
| Ex. 1 | 0.0014 | 0.0002 | 0.0021 | 0.0015 | 100 | 2.26 |
| Ex. 2 | 0.0092 | 0.0027 | 0.0043 | 0.0380 | 100 | 0.313 |
| C. Ex. 1 | 0.0214 | 0.0027 | 0.0053 | 0.0036 | 100 | 6.69 |

TEST EXAMPLE 1

Evaluation of Corrosion Rate of Biodegradable Implant Comprising Mg Alloy

The biodegradable implants of Examples 1 and 2 and Comparative Example 1 were immersed in a solution having a composition of Table 2 below, and thus the corrosion rate was evaluated based on the hydrogen evolution amount in relation to the immersion time. The results are shown in FIG. 1.

TABLE 2

|  | Molar Concentration [mM/L] | Mass [g] |
| --- | --- | --- |
| CaCl$_2$ 2H$_2$O | 1.26 | 0.185 |
| KCl | 5.37 | 0.400 |
| KH$_2$PO$_4$ | 0.44 | 0.060 |
| MgSO$_4$·7H$_2$O | 0.81 | 0.200 |
| NaCl | 136.89 | 8.000 |
| Na$_2$HPO$_4$ 2H$_2$O | 0.34 | 0.060 |
| NaHCO$_3$ | 4.17 | 0.350 |
| D-Glucose | 5.55 | 1.000 |

With reference to FIG. 1, in Example 1, hydrogen began to occur after 50 hours, and in Example 2, hydrogen was not almost generated from initial immersion to after 200 hours, and thus the implant was slightly corroded. However, in Comparative Example 1, hydrogen was generated from initial immersion. Hence, the biodegradation rate of the biodegradable implants of Examples 1 and 2 satisfying the following condition: 0<{Fe+Ni}/Mn≤5 was slower than that of Comparative Example 1 satisfying the following condition: {Fe+Ni}/Mn>5

EXAMPLES 3 TO 11 AND COMPARATIVE EXAMPLES 2 to 5

Manufacturing of Biodegradable Implant

Mg, Ca, Mn and Zn in the amounts shown in Table 3 below were charged in a crucible having an inner diameter of 50 mm made of stainless steel (SUS 410). Subsequently, while Ar gas was allowed to flow around the crucible so that Mg, Ca, Mn and Zn in the crucible did not come into contact with air, the temperature of the crucible was increased to about 700~750° C. inside a resistance heating furnace so that the Mg, Ca, and Mn melted. The crucible was stirred so that the molten Mg, Ca, and Mn were well mixed. The completely molten Mg alloy was cooled, thus preparing an Mg alloy in the solid phase. Also upon cooling, the crucible was immersed in water to enhance the mechanical strength of Mg, whereby the molten Mg alloy was rapidly cooled.

The Mg alloy in the solid phase was extruded at 400° C. under conditions of the ratio of reduction in the cross-sectional area before and after extrusion (the extrusion ratio) being set to 15:1.

TABLE 3

|  | Mg (wt %) | Ca (wt %) | Mn (wt %) | Zn (wt %) |
| --- | --- | --- | --- | --- |
| Ex. 3 | 89 | 10 | 1 | — |
| Ex. 4 | 88.98 | 9.99 | — | 1.03 |
| Ex. 5 | 86.29 | 10.8 | — | 2.91 |
| Ex. 6 | 84.42 | 10.7 | — | 4.88 |
| Ex. 7 | 94.88 | 4.62 | — | 0.50 |
| Ex. 8 | 94.52 | 4.72 | — | 0.76 |
| Ex. 9 | 93.86 | 4.51 | — | 1.63 |
| Ex. 10 | 92.44 | 4.56 | — | 3.00 |
| Ex. 11 | 91.23 | 4.65 | — | 4.12 |
| C. Ex. 2 | 95 | 5 | — | — |
| C. Ex. 3 | 89.9 | 10.1 | — | — |
| C. Ex. 4 | 100 | | | |
| C. Ex. 5 | AZ91: Al: 8.5~9.5%, Zn: 0.45~9%, Mg: the remainder | | | |

Mg: purity 99.98% Mg, MP21-31-31 (available from TIMMINCO)

TEST EXAMPLE 1

Evaluation of Mechanical Strength of Biodegradable Implant Using Mg Alloy

Figure 2:
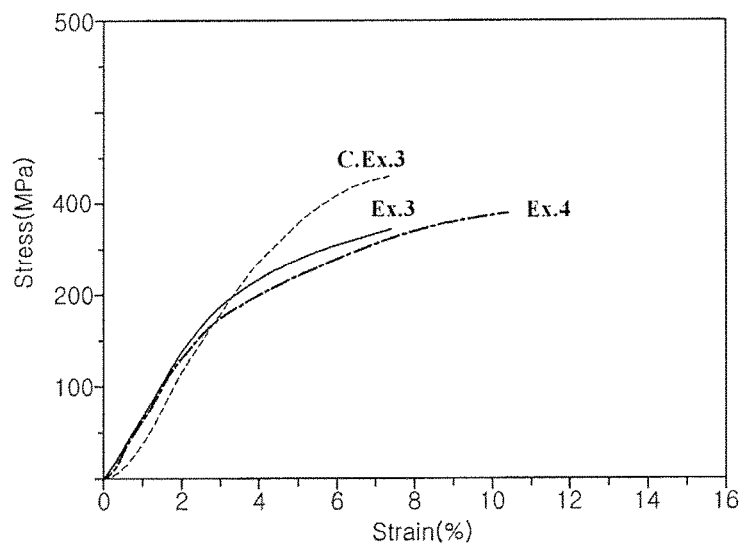
FIG. 2 is a graph showing results of evaluating mechanical strength of the implant samples of Examples 3 and 4 and Comparative Example 3 before extrusion.
Figure 3:
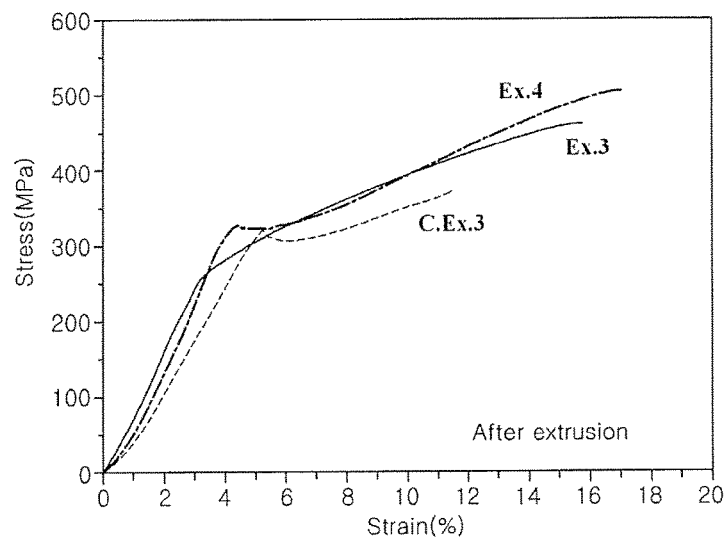
FIG. 3 is a graph showing results of evaluating mechanical strength of the implant samples of Examples 3 and 4 and Comparative Example 3 after extrusion.

FIG. 2 shows results of evaluating mechanical strength of the biodegradable implant before extrusion, and FIG. 3 shows results of evaluating mechanical strength of the biodegradable implant before extrusion.

With reference to FIGS. 2 and 3, before extrusion, Example 3 had a yield strength of 180 Mpa, which was slightly lower than 220 MPa of Comparative Example 3, and also after extrusion, Example 3 had 280 MPa which was slightly lower than 320 MPa of Comparative Example 3. However, because 280 MPa is a value that is sufficiently applicable to implant products that undergo loads, the corresponding implant may be reasonably applied to products. Also, the elongation did not reach 7~10% before extrusion and was increased to 12~16% after extrusion. This means that performance in terms of enduring a strong external impact is superior.

Example 4 had a strength of 170 Mpa which was lower than 220 MPa, but maintained 320 Mpa equal to that of Comparative Example 3 after extrusion. The elongation was increased from 12% before extrusion to 17% after extrusion and thus mechanical properties were equal to or better than those of Comparative Example 3.

Here, the yield strength refers to the strength at the point in time at which the gradient changes in each graph.

TEST EXAMPLE 2

Evaluation of Corrosion Rate of Biodegradable Implant Using Mg Alloy

The biodegradable implants of Examples 3 to 11 and Comparative Examples 3 to 6 were immersed in a biomimetic solution having a composition of Table 2, and thus the corrosion rate was evaluated based on the hydrogen evolution rate in relation to the immersion time. This is because the corrosion rate of an implant is typically determined from the hydrogen evolution rate in the biomimetic solution because hydrogen is generated upon the biodegradation of Mg.

Figure 4:
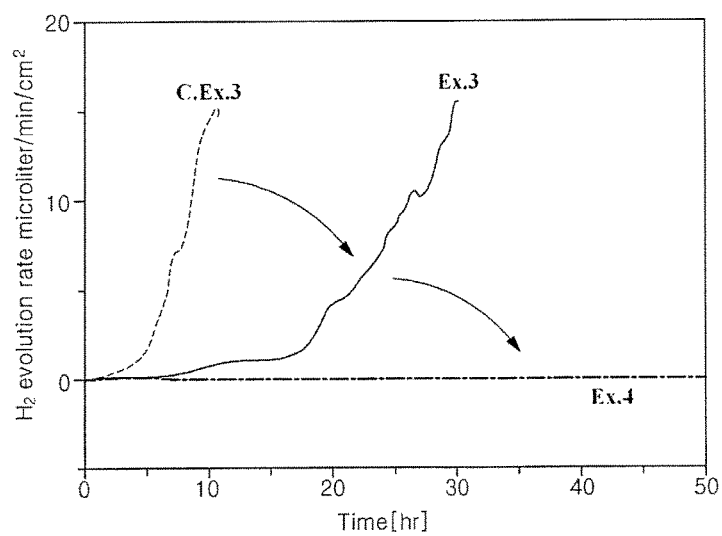
FIG. 4 is a graph showing the hydrogen evolution rate in relation to the immersion time of the implant samples of Examples 3 and 4 and Comparative Example 3.
Figure 5:
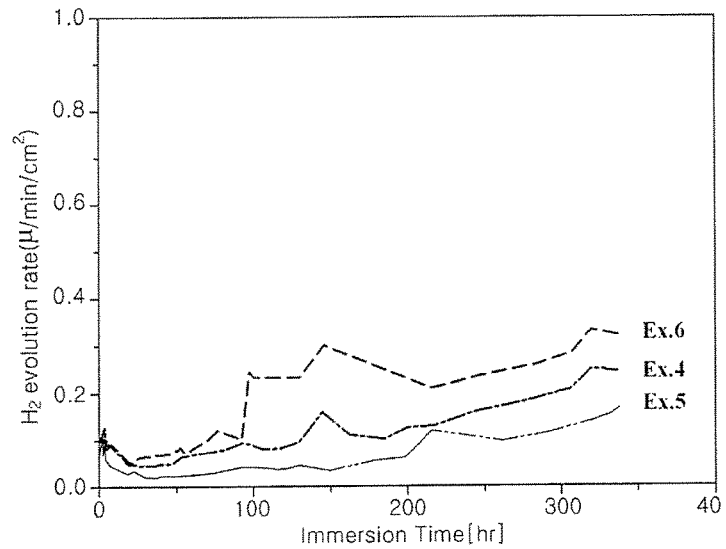
FIG. 5 is a graph showing the hydrogen evolution rate in relation to the immersion time of the implant samples of Examples 4 to 6.
Figure 6:
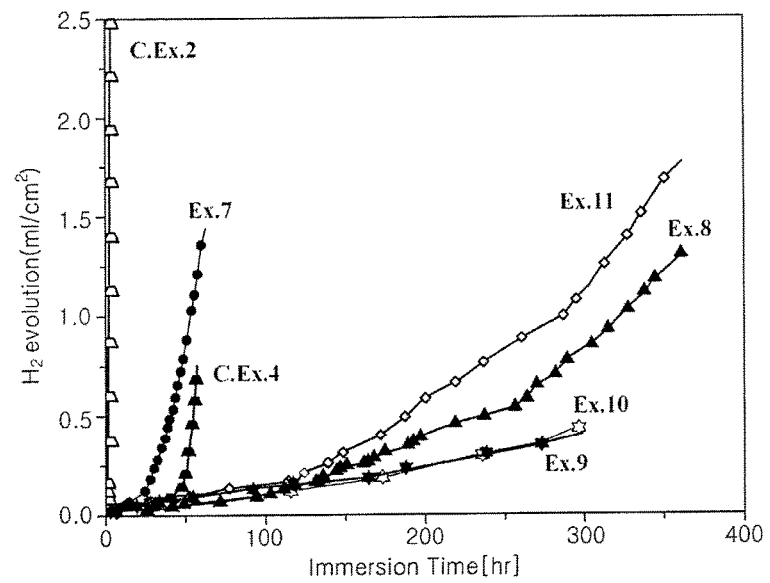
FIG. 6 is a graph showing the hydrogen evolution amount in relation to the immersion time of the implant samples of Examples 7 to 11 and Comparative Examples 2 and 4.
Figure 7:
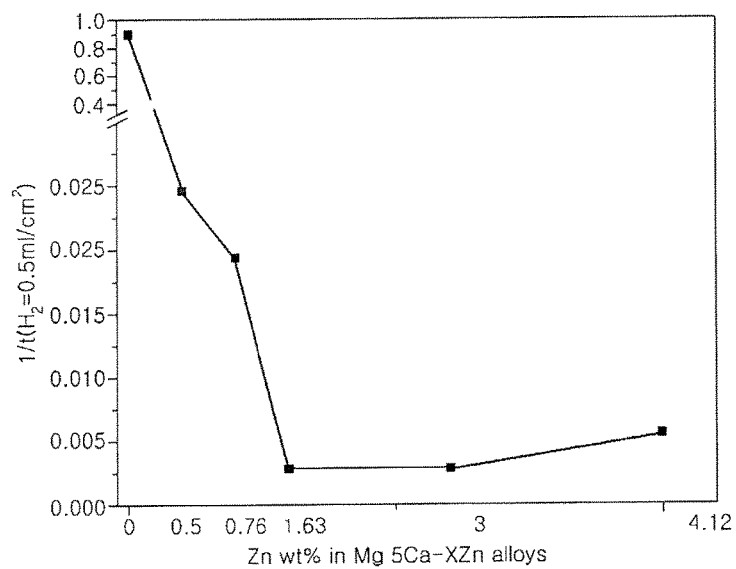
FIG. 7 is a graph showing the hydrogen evolution amount in relation to Zn content.

FIG. 4 is a graph showing the hydrogen evolution rate in relation to the immersion time in Examples 3 and 4 and Comparative Example 3. FIG. 5 is a graph showing the hydrogen evolution rate in relation to the immersion time in Examples 4 to 6 before extrusion. FIG. 6 is a graph showing the hydrogen evolution amount in relation to the immersion time in Examples 7 to 11 and Comparative Examples 2 and 4 before extrusion. FIG. 7 is a graph showing the hydrogen evolution amount in relation to the Zn content.

With reference to FIG. 4, in Comparative Example 3, rapid decomposition began to occur after 5 hours, but in Example 3 rapid decomposition began to occur after 17 hours. In Example 4, 30 days after immersion, drastic corrosion did not take place. Thus the biodegradable implants according to the present invention exhibited superior corrosion resistance compared to Comparative Example 3.

With reference to FIGS. 5 and 6 showing the corrosion rate in relation to the Zn content, the corrosion rate was increased in proportion to an increase in the Zn content.

With reference to FIG. 7, the corrosion rate in relation to the Zn content was represented when the hydrogen evolution amount was 0.5 ml/cm$^2$. In terms of the corrosion rate, the optimal composition of the present alloy was 0.1~5% and preferably 0.1~3%. The reason is that the corrosion rate zone is the same, but the low Zn content is regarded as good on the assumption of the same corrosion rate in light of the side effects that Zn has on the human body.

On the axis x, 0.5 designates Example 7, 0.76 designates Example 8, 1.63 designates Example 9, 3 designates Example 10, and 4.12 designates Example 11.

Figure 8:
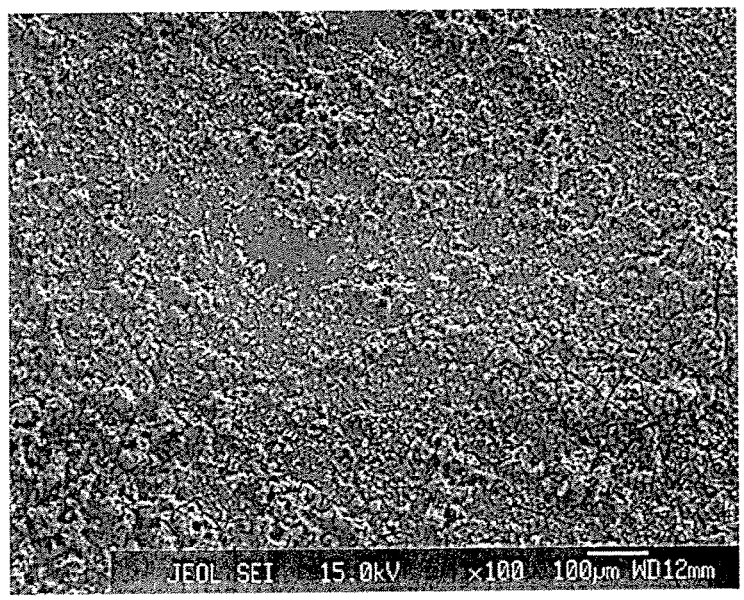
FIG. 8 is an electron microscope image showing the surface of the implant sample of Example 7 immersed in a biomimetic solution for 61 hours.
Figure 9:
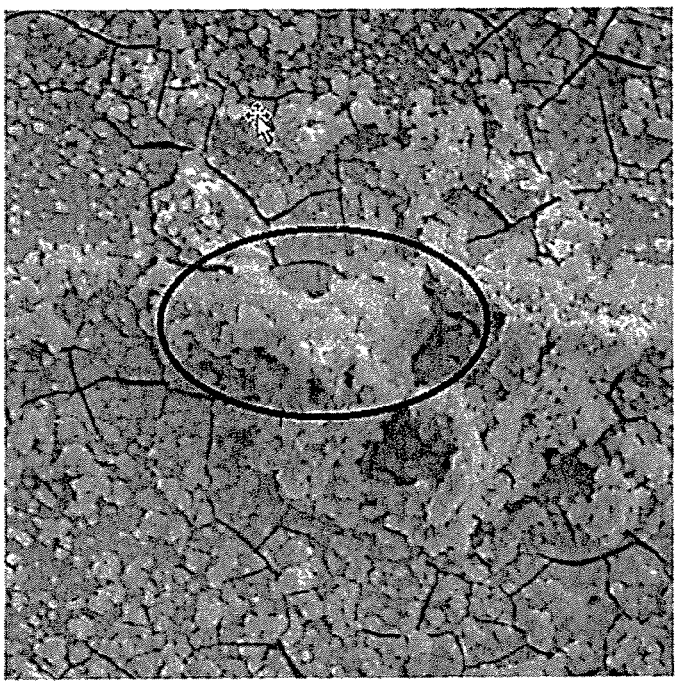
FIG. 9 is an image showing the surface of the implant sample of Example 7 immersed in a biomimetic solution for 61 hours as analyzed using EDS.
Figure 10:
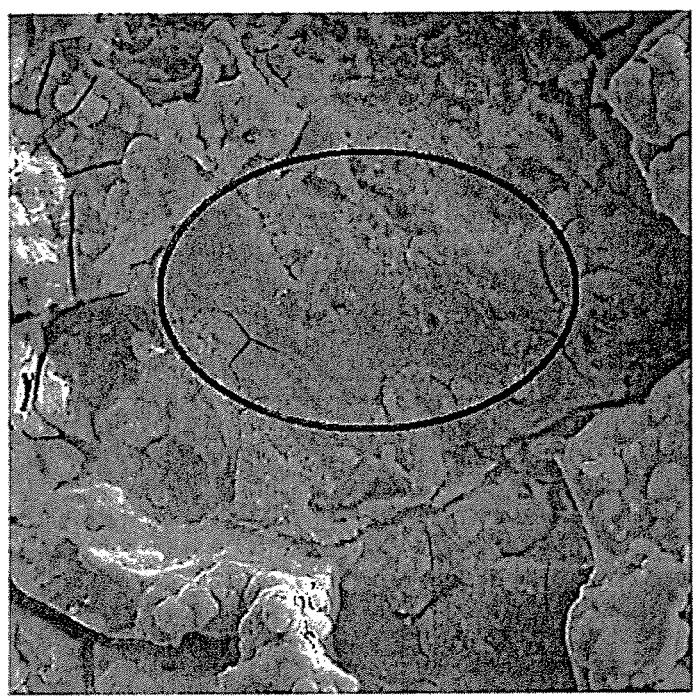
FIG. 10 is an image showing the implant sample of Example 7 which is immersed in a biomimetic solution for 61 hours and from which a corrosion material was removed.

FIG. 8 is an electron microscope image showing the surface of the implant sample of Example 7 immersed in the biomimetic solution for 61 hours, and FIG. 9 is an EDS image showing the surface of the implant sample of Example 7. FIG. 10 is an image showing the implant sample of Example 7 from which the corrosion material was removed.

With reference to FIGS. 8 and 9, the corrosion material was produced on the surface. The components of the corrosion material are given in Table 4 below.

TABLE 4

| Component | Mass (%) | Atom (%) |
|---|---|---|
| O | 33.076 | 52.0767 |
| Mg | 5.580 | 5.7816 |
| P | 19.398 | 15.7781 |
| Ca | 41.946 | 26.3635 |
| Total | 100.000 | 100.0000 |

As is apparent from Table 4, oxygen was measured as a component of the corrosion material, from which the implant sample of Example 7 was oxidized, and phosphorus and calcium were derived from the biomimetic solution. Thus due to the corrosion material including phosphorus and calcium, bone binding effects could be increased.

FIG. 10 shows the implant sample from which the corrosion material shown in FIGS. 8 and 9 was removed. The results of analyzing the implant sample of Example 7 having no corrosion material are shown in Table 5 below.

TABLE 5

| Component | Mass (%) | Atom (%) |
|---|---|---|
| O | 7.749 | 11.4133 |
| Mg | 90.178 | 87.4252 |
| P | 0.521 | 0.3968 |
| Ca | 0.903 | 0.5305 |
| Zn | 0.649 | 0.2342 |
| Total | 100.000 | 100.0000 |

With reference to Table 5, even after the corrosion material was removed, phosphorus and calcium are left behind. Like this, phosphorus and calcium derived from the biomimetic solution were not easily removed.

Figure 11:
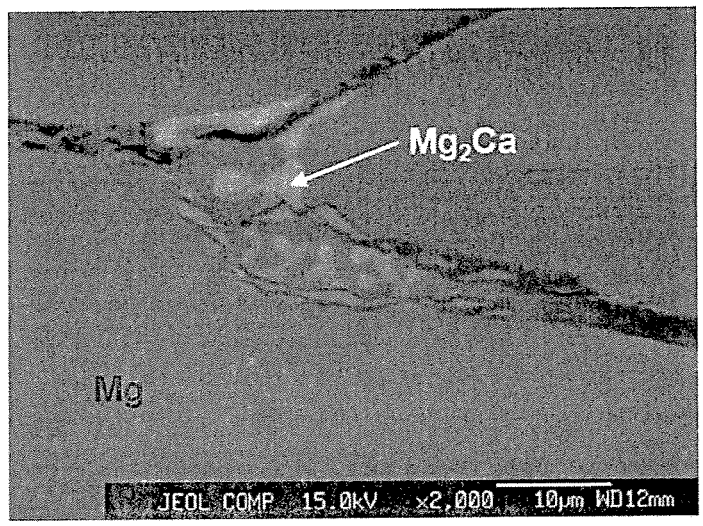
FIG. 11 is an image showing the cross-section of the implant sample of Example 7 immersed in a biomimetic solution for 61 hours.
Figure 12:
FIG. 12 is an enlarged image of the image of FIG. 11.
Figure 13:
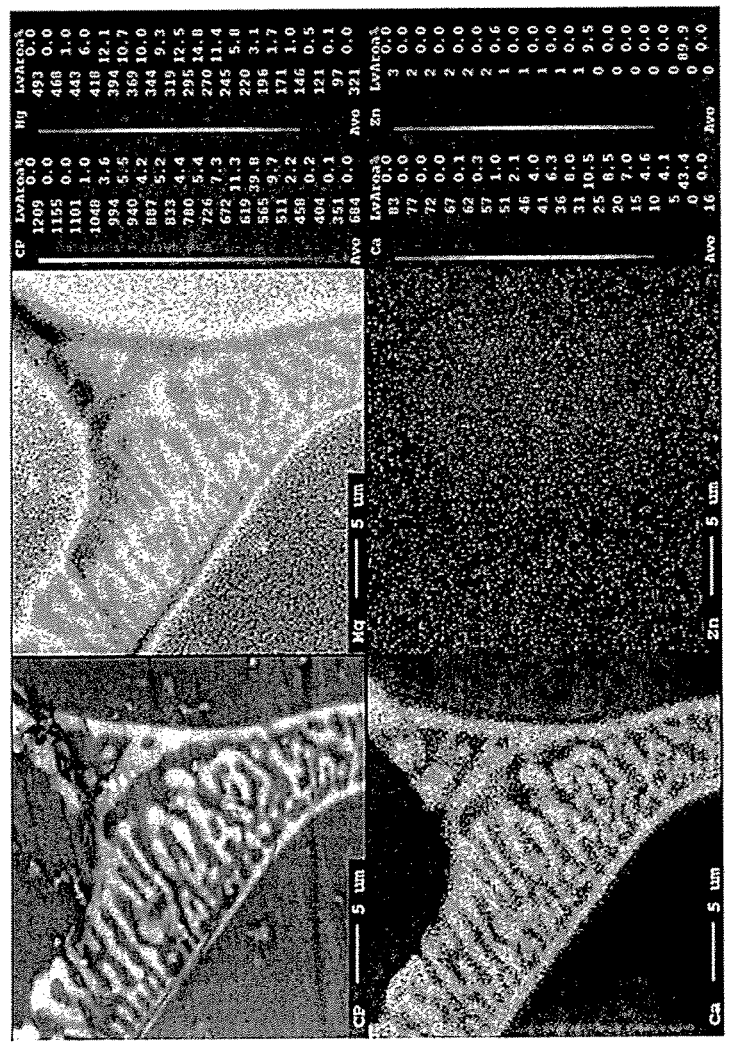
FIG. 13 is of WDS (AA-8500F, available from JEOL) images showing the implant sample of Example 7 immersed in a biomimetic solution for 61 hours.

FIG. 11 is an image showing the cross-section of the implant sample of Example 7 immersed in the biomimetic solution for 61 hours, FIG. 12 is an enlarged image of the image of FIG. 11, and FIG. 13 is of WDS (JXA-8500F, available from JEOL) images showing the implant sample of Example 7 immersed in the biomimetic solution of Table 2 for 61 hours.

With reference to FIGS. 11 to 13, the bright line region in Mg designates Mg$_2$Ca, and the dark line region designates a corroded portion. The corrosion was observed to progress while the black line gradually penetrated in Mg.

Figure 14:
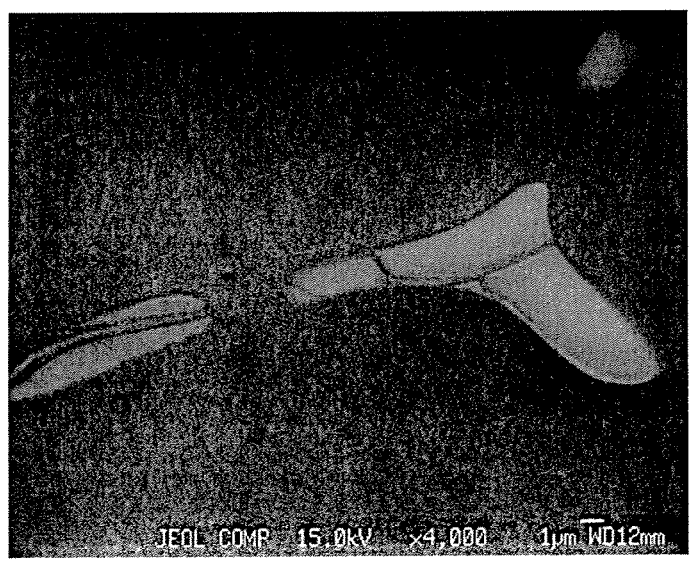
FIG. 14 is an image showing the cross-section of the implant sample of Example 8 immersed in a biomimetic solution for 61 hours.

FIG. 14 is an image showing the cross-section of the implant sample of Example 8 immersed in the biomimetic solution for 61 hours.

Figure 15:
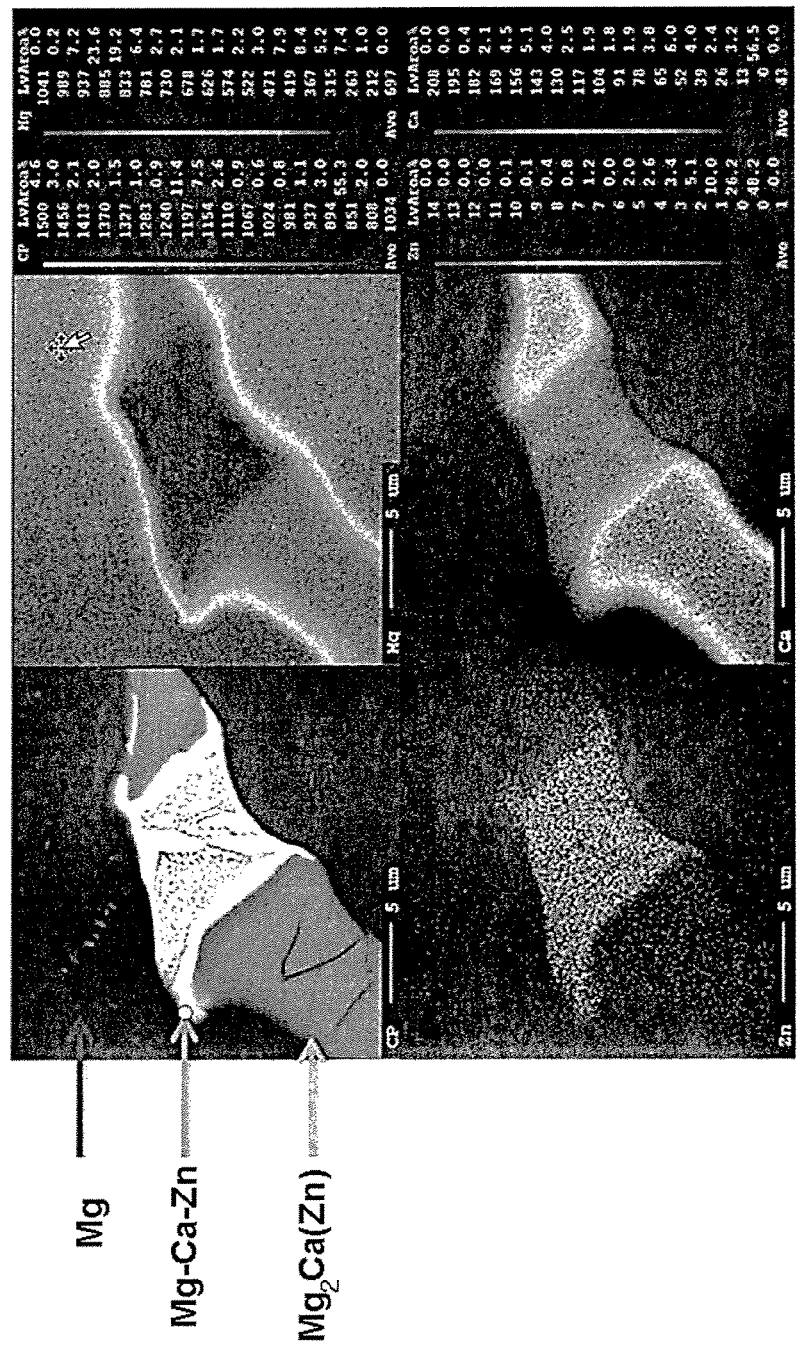
FIG. 15 is of WDS (DCA-8500F, available from JEOL) images showing the implant sample of Example 8 immersed in a biomimetic solution for 61 hours.

FIG. 15 is of WDS (JXA-8500F, available from JEOL) images showing the implant sample of Example 8 immersed in the biomimetic solution for 61 hours.

With reference to FIGS. 14 and 15, Mg$_2$Ca(Zn) was enclosed with the Mg—Ca—Zn compound. When the Zn content was increased, Zn was further contained in Mg$_2$Ca.

TEST EXAMPLE 3

Evaluation of Corrosion Rate of Biodegradable Implant Using Mg Alloy

The yield strength, fracture strength and the elongation of the implant samples of Examples 7 to 11 and Comparative Example 2 were measured. The results are shown in Table 6 below.

TABLE 6

| | Yield Strength/Fracture Strength | Elongation (%) |
|---|---|---|
| Ex. 7 | 84 ± 3/180 ± 10 | 11.8 ± 0.4 |
| Ex. 8 | 107 ± 2/240 ± 15 | 13.9 ± 1.5 |
| Ex. 9 | 97 ± 2/203 ± 10 | 9.5 ± 1 |
| Ex. 10 | 103 ± 2/255 ± 14 | 12.2 ± 0.6 |
| Ex. 11 | 109 ± 2/247 ± 11 | 14.6 ± 2 |
| C. Ex. 2 | 87 ± 3/180 ± 10 | 10.5 ± 0.3 |

TEST EXAMPLE 4

Evaluation of Corrosion Rate Upon Applying Ultrasound to Biodegradable Implant Using Mg Alloy The implant sample of Example 8 was cut to a width of 9.65 cm, a length of 19.66 cm, and a thickness of 1.18 cm, thus preparing two samples. Ultrasound was applied to two samples, and then the samples were immersed in the biomimetic solution of Table 2 for 3 hours and the hydrogen evolution amount was measured. The results are shown in FIGS. 15 and 16.

Figure 16:
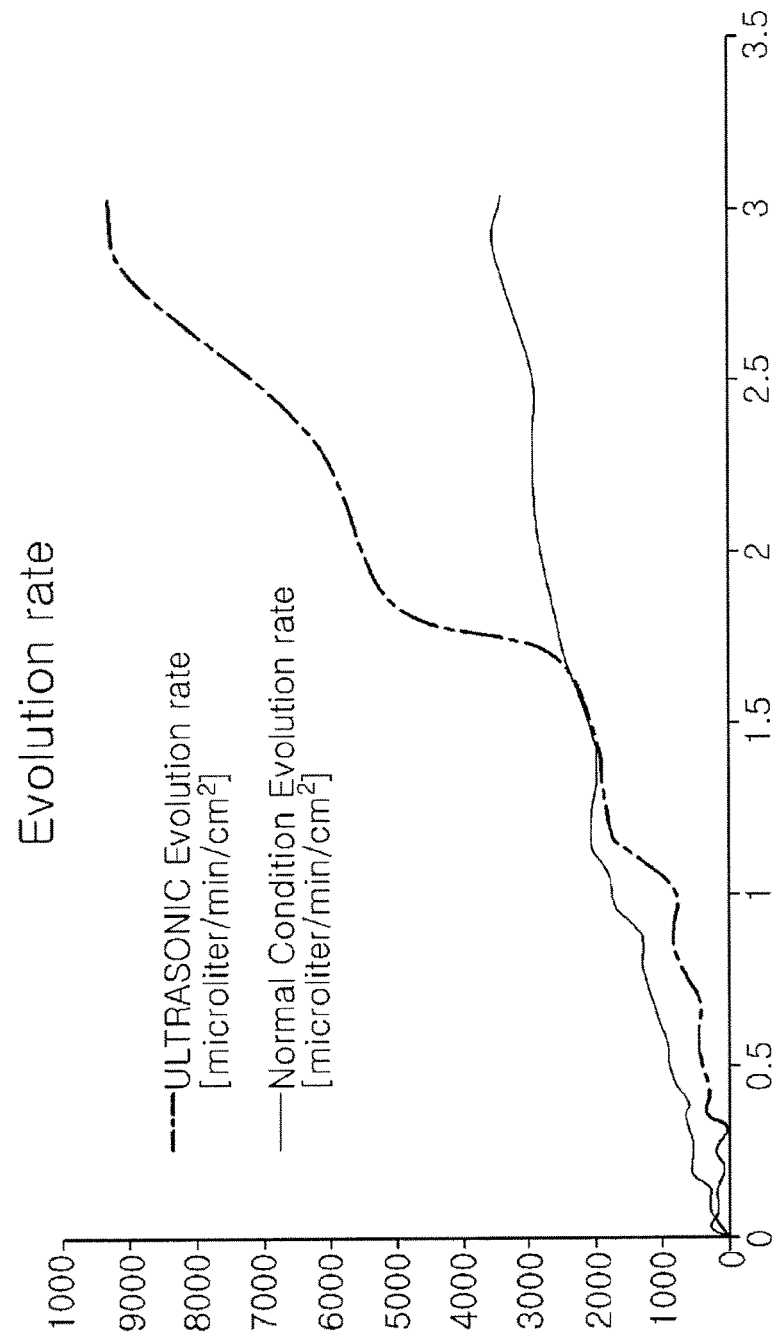
FIG. 16 is a graph showing the hydrogen evolution rate in relation to the immersion time in two implant samples of Example 8 one of which is treated with ultrasound and the other one of which is not treated with ultrasound after which they are immersed in a biomimetic solution.
Figure 17:
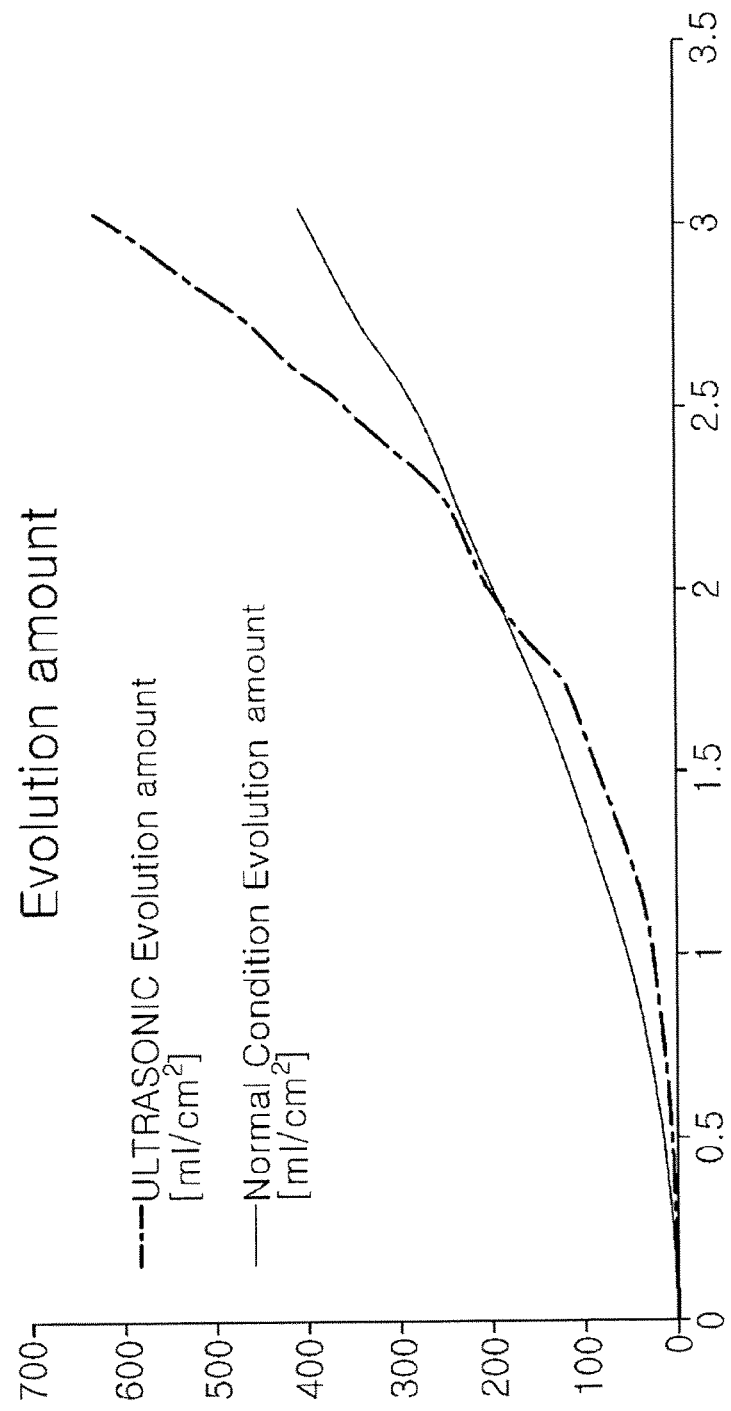
FIG. 17 is a graph showing the hydrogen evolution amount in relation to the immersion time in the implant sample of Example 8 treated with ultrasound and then immersed in a biomimetic solution.

With reference to FIGS. 16 and 17, the sample to which ultrasound was applied generated a large amount of hydrogen, and thus was more quickly corroded.

EXAMPLES 12 to 14

Manufacturing of Biodegradable Implant

Mg and Mn in the amounts shown in Table 7 below were charged in a crucible having an inner diameter of 50 mm that was made of stainless steel (SUS 410). Subsequently, while Ar gas was allowed to flow around the crucible so that Mg and Mn in the crucible did not come into contact with air, the temperature of the crucible was increased to about 700~750° C. inside a resistance heating furnace, so that the Mg and Mn melted. The crucible was stirred so that the molten Mg and Mn were well mixed. The completely molten Mg alloy was cooled, thus preparing an Mg alloy in the solid phase. Also upon cooling, the crucible was immersed in water to enhance the mechanical strength of Mg, whereby the molten Mg alloy was rapidly cooled, resulting in a biodegradable implant

TABLE 7

|  | Mg (wt %) | Mn (wt %) |
| --- | --- | --- |
| Ex. 12 | Remainder | 0.0015 |
| Ex. 13 | Remainder | 0.097 |
| Ex. 14 | Remainder | 0.51 |

Mg: purity 99.98% Mg, MP21-31-31 (available from TIMMINCO)

TEST EXAMPLE 5

Evaluation of Corrosion Rate of Biodegradable Implant in Relation to Controlled Mn Content The implant samples of Examples 12 to 14 were cut to a width of 9.65 cm, a length of 19.66 cm, and a thickness of 1.18 cm, thus preparing two samples. Ultrasound was applied to the two samples, after which the samples were immersed in the biomimetic solution of Table 2 for 3 hours, and the hydrogen evolution amount was measured. The results are shown in FIG. 18.

Figure 18:
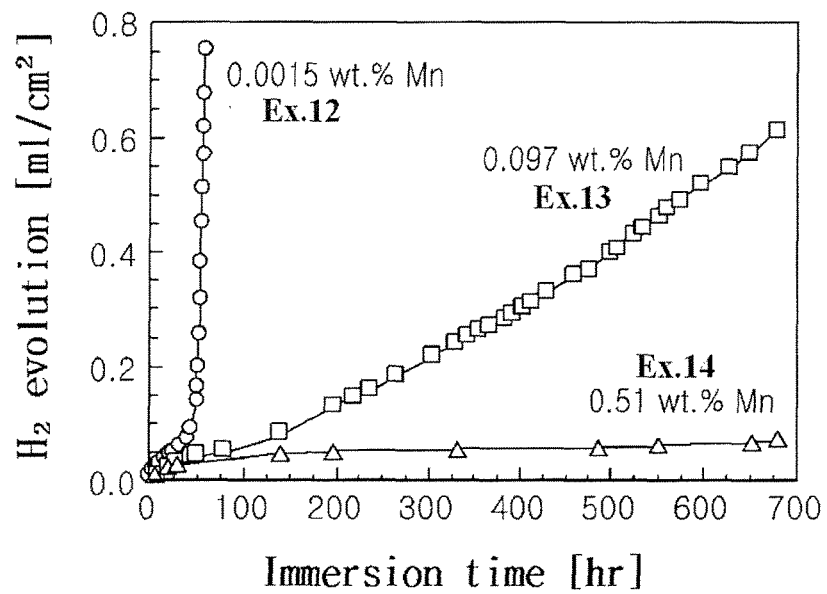
FIG. 18 is a graph showing the hydrogen evolution amount in relation to the immersion time of the implant samples of Examples 12~14.

With reference to FIG. 18, when Mn was added in an amount of 1 wt % or less but exceeding 0 wt %, corrosion began to occur after 50 hours. Corrosion properties were the most efficiently controlled when Mn was added in an amount of 0.5 wt % or more.

TEST EXAMPLE 6

Evaluation of Corrosion Rate of Extruded Biodegradable Implant

The biodegradable implant of Example 14 was extruded at 400° C., and the ratio of reduction in the cross-sectional area before and after extrusion (the extrusion ratio) was set to 25:1.

The biodegradable implant of Example 14 before and after extrusion was immersed in the biomimetic solution of Table 2 for 3 hours and the hydrogen evolution amount was measured.

Figure 19:
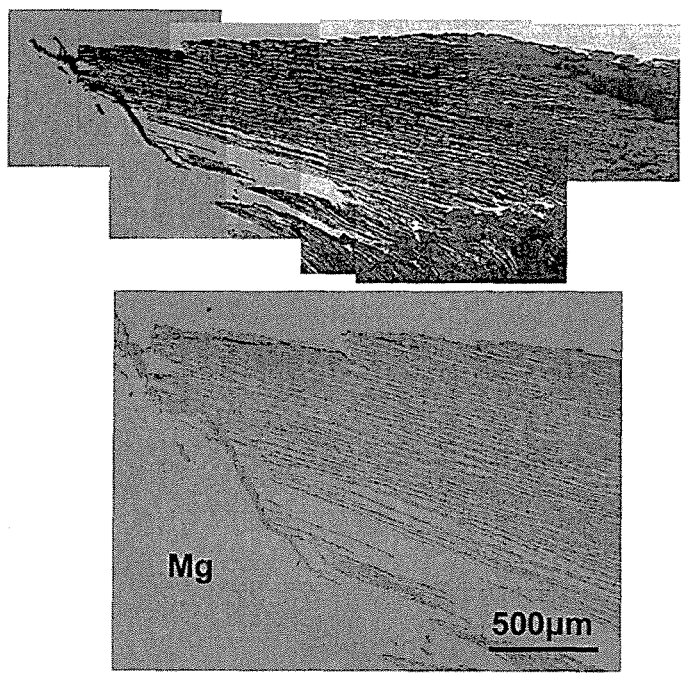
FIG. 19 is of images showing the size of crystal grains of the implant sample of Example 14 before extrusion.

FIG. 19 is of images showing the crystal grains when the biodegradable implant of Example 14 was not extruded.

With reference to FIG. 19, PCP occurred along the crystal grains.

Figure 20:
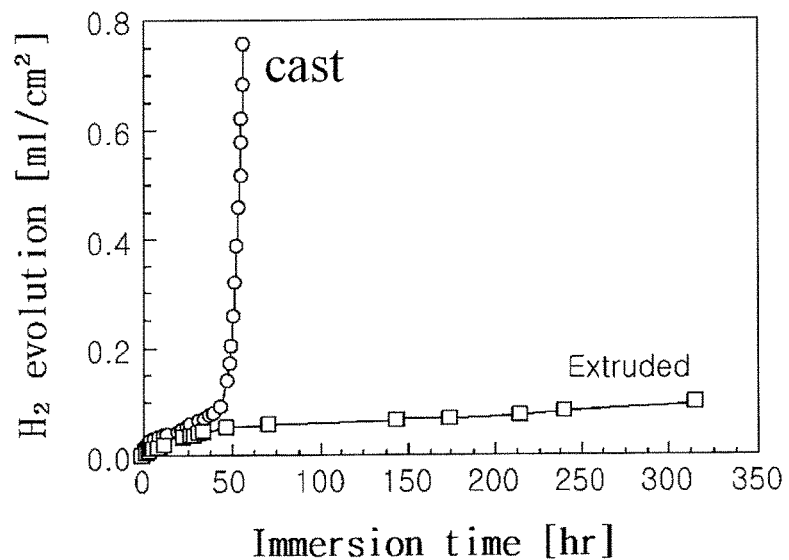
FIG. 20 is a graph showing the hydrogen evolution amount in relation to the immersion time before and after extrusion of the implant sample of Example 14.

FIG. 20 is a graph showing corrosion properties of the biodegradable implant of Example 14 before and after extrusion.

With reference to FIG. 20, when extrusion was not performed, corrosion properties were deteriorated.

EXAMPLE 15

Manufacturing of Biodegradable Implant

Mg and MgO in the amounts shown in Table 8 below were charged in a crucible having an inner diameter of 50 mm made of stainless steel (SUS 410). Subsequently, while Ar gas was allowed to flow around the crucible so that Mg and MgO in the crucible did not come into contact with air, the temperature of the crucible was increased to about 700~750° C. inside a resistance heating furnace, so that the Mg and MgO melted. The crucible was stirred so that the molten Mg and MgO were well mixed. The completely molten Mg alloy was cooled, thus preparing an Mg alloy in the solid phase. Also upon cooling, the crucible was immersed in water to enhance the mechanical strength of Mg, whereby the molten Mg alloy was rapidly cooled, resulting in a biodegradable implant

TABLE 8

|  | Mg (wt %) | MgO (wt %) |
| --- | --- | --- |
| Ex. 15 | Remainder | 10 |

Mg: purity 99.98% Mg, MP21-31-31 (available from TIMMINCO)

TEST EXAMPLE 7

Evaluation of Hydrogen Evolution Amount of Biodegradable Implant Comprising MgO In Vivo The biodegradable implant samples of Example 15 and Comparative Example 4 were inserted into a rat to evaluate the hydrogen evolution amount in vivo.

Figure 21:
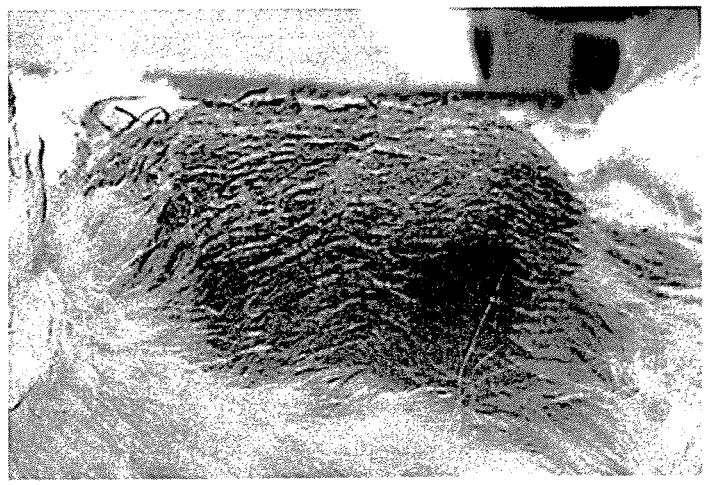
FIG. 21 is a photograph showing swelling due to the generation of hydrogen gas in a rat into which the implant sample of Comparative Example 4 is inserted.

FIG. 21 is a photograph showing the rat having the biodegradable implant sample of Comparative Example 4 inserted therein.

With reference to FIG. 21, hydrogen was generated in the rat, thus causing swelling.

However, when the biodegradable implant sample of Example 15 was inserted into the rat, there was no swelling.

The invention claimed is:

1. A biodegradable implant in the form of a composite material, comprising a structure having pores, wherein at least some of the pores contain a magnesium alloy of from 4.51 wt % to 10.8 wt % of Ca;
   from 0.76 to 4.12 wt % of Zn;
   and a remainder of Mg.

2. The biodegradable implant of claim 1, wherein the magnesium alloy is charged in the pores of a porous structure.

3. The biodegradable implant of claim 2, wherein the porous structure has a porosity of 5~95%.

4. The biodegradable implant of claim 2, wherein the porous structure comprises one selected from the group consisting of a metal, a ceramic and a polymer.

5. The biodegradable implant of claim 4, wherein the metal comprises one or more selected from the group consisting of titanium or a titanium alloy, a cobalt-chromium alloy, and stainless steel.

6. The biodegradable implant of claim 4, wherein the ceramic comprises one or more selected from the group consisting of calcium phosphate, alumina, zirconia, and magnesia.

7. The biodegradable implant of claim 4, wherein the polymer comprises one or more selected from the group consisting of polyethylene, polylactic acids (PLA), polyglycolic acid (PGA), and a copolymer thereof including PLGA.

8. The biodegradable implant of claim 1, which is configured for use in one selected from the group consisting of orthopedics, dental care, plastic surgery and blood vessels.

9. The biodegradable implant of claim 4, wherein the metal comprises a titanium alloy.

10. The biodegradable implant of claim 1, in the form of an orthopedic device.

11. A biodegradable medical implant in the form of a composite material, comprising a structure having pores, wherein at least some of the pores are filled with a magnesium alloy of from 4.51 wt % to 10.8 wt % of Ca; from 0.76 to 4.12 wt % of Zn; and a remainder of Mg.

12. The biodegradable implant according to claim 1, wherein the pores are filled with a magnesium alloy of from 4.51 wt % to 10.8 wt % of Ca; from 0.76 to 4.12 wt % of Zn; and a remainder of Mg.

13. The biodegradable medical implant according to claim 11, wherein the pores are filled with a magnesium alloy of from 4.51 wt % to 10.8 wt % of Ca; from 0.76 to 4.12 wt % of Zn; and a remainder of Mg.

* * * * *